(12) United States Patent
Kiehm et al.

(10) Patent No.: US 8,865,879 B2
(45) Date of Patent: Oct. 21, 2014

(54) CHITOSAN BEADS AND FILLER COMPRISING SUCH BEADS

(75) Inventors: Kevin Kiehm, Frankfurt am Main (DE); Bernhard Hauptmeier, Geinhausen (DE); Peter Boderke, Schwalbach (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

(21) Appl. No.: 13/639,004

(22) PCT Filed: Apr. 7, 2011

(86) PCT No.: PCT/EP2011/001736
§ 371 (c)(1),
(2), (4) Date: Dec. 12, 2012

(87) PCT Pub. No.: WO2011/124380
PCT Pub. Date: Oct. 13, 2011

(65) Prior Publication Data
US 2013/0090306 A1    Apr. 11, 2013

Related U.S. Application Data

(60) Provisional application No. 61/321,950, filed on Apr. 8, 2010.

(30) Foreign Application Priority Data

Apr. 8, 2010    (EP) .................... 10003795

(51) Int. Cl.
| | | |
|---|---|---|
| C08B 37/08 | (2006.01) | |
| A61K 9/16 | (2006.01) | |
| A61L 31/04 | (2006.01) | |
| A61L 27/20 | (2006.01) | |

(52) U.S. Cl.
CPC ............ *A61L 27/20* (2013.01); *A61K 9/1652* (2013.01); *A61L 31/042* (2013.01)
USPC .......................................... 536/20; 536/18.7

(58) Field of Classification Search
None
See application file for complete search history.

(56) References Cited

FOREIGN PATENT DOCUMENTS

| CN | 101245238 | 8/2008 |
|---|---|---|
| JP | 2005068282 | 3/2005 |
| WO | WO2008/103594 | 8/2008 |

OTHER PUBLICATIONS

Chen et al. International Journal of Pharmaceutics (2008), vol. 349, pp. 180-187.*
Chemical Abstracts Service, 2005, Database XP002599725, H. Ishikawa, "Chitosan Microparticles, Their Manufacture, and Formation of Chitosan Films or Fivers From Them".
X.Z. Shu, et al., International Journal of Pharmaceutics, vol. 233, p. 217-225, 2002.
X.Z. Shu, et al., Journal Microencapsulation, vol. 18, No. 2, p. 237-245, 2001.

* cited by examiner

*Primary Examiner* — Patrick Lewis
(74) *Attorney, Agent, or Firm* — Hueschen and Sage

(57) ABSTRACT

The present invention pertains to chitosan beads consisting of chitosan cross-linked with citrate ions. The present invention furthermore pertains to a filler comprising such chitosan-citrate beads. In one embodiment of the instant invention the filler is a dermal filler. In one further embodiment of the present invention the dermal filler is for the treatment of wrinkles and/or folds. In another embodiment of the instant invention the filler is for use in the treatment of a medical condition. The filler provided in the present invention may further comprise one or more active pharmaceutical ingredients. Further, the present invention pertains to a process for preparing the filler as claimed herein.

4 Claims, 1 Drawing Sheet

Chitosan beads cross-linked with citrate ions and stored in citrate buffer. Bead size is 1.0 to 1.5 mm.
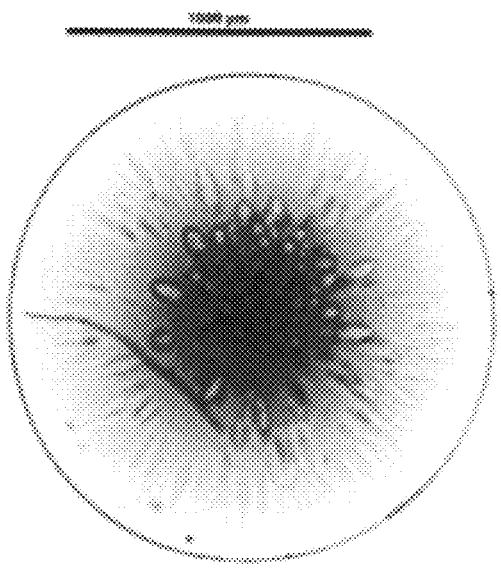

CHITOSAN BEADS AND FILLER COMPRISING SUCH BEADS

FIELD OF THE INVENTION

The present invention pertains to chitosan beads consisting of chitosan cross-linked with citrate ions. The present invention furthermore pertains to a filler comprising such chitosan-citrate beads. In one embodiment of the instant invention the filler is a dermal filler. In one further embodiment of the present invention the dermal filler is for the treatment of wrinkles and/or folds. In another embodiment of the instant invention the filler is for use in the treatment of a medical condition. The filler provided in the present invention may further comprise one or more active pharmaceutical ingredients. Further, the present invention pertains to a process for preparing the filler as claimed herein.

BACKGROUND OF THE INVENTION

Treatment with fillers is known since 1980s. Today's most preferred fillers can be classified as hyaluronic acid-based fillers (Hylaform®, Hylaform® Plus, Restylane®, Perlane®, Juvederm®, Juvederm® Ultra, Juvederm® Ultra Plus, Puragen®, Puragen® Plus, Matridur®), collagen based fillers (Zyderm® I, Zyderm® II, Zyplast®, Atelocollagen®, CosmoDerm® I, CosmoDerm® II, Resoplast®) and alginate based fillers (e.g. Novabel®) as described in DE 10 2004 019 241.

Collagen is a natural protein of connective tissue. However, some people suffer from allergic reactions to collagen and thus, an allergy test is always suggested by the practitioner prior to injection of fillers comprising collagen. Hyaluronic acid is a polysaccharide and is naturally found in many tissues of the body. The unfavorable effect of fillers comprising hyaluronic acid is the short-lasting result and the need for multiple injections for an observable effect. Thereby swellings can occur, which decay in 1-3 days. Thus, treatments with collagen and hyaluronic acid based fillers are costly and painful due to the prerequisite of multiple injections and allergy tests. Further reported complications for the fillers is poor syringeability due to high viscosity, aggregation of the particles in the packaging and non-homogeneous distribution of the particles at the injection site.

The use of alginate as filler is known from DE 10 2004 019 241. However, DE 10 2004 019 241 suggests for the long-lasting effect of the cross-linked alginate particles the use of barium (paragraph [0031]).

Therefore, there remains a continuous need for an improved dermal filler with an improved safety profile, an improved tolerability profile, improved application characteristics, and a long-lasting effect.

Chitosan and its derivatives are very well known natural substances and have been employed in the formulation of controlled release systems, i.e. microcapsules and similar colloidal delivery systems. This is documented in several publications, e.g. M. Prabaharan "*Review Paper: Chitosan derivatives as promising materials for controlled drug delivery*" *Journal of Biomaterials Applications,* 2008; 23; 5 and in O. Gaserod et al. "*Microcapsules of alginate-chitosan—I A quantitative study of the interaction between alginate and chitosan*" *Biomaterials* 19 (1998), 1815-1825; and in Cai et al. "*Biodegradable chitosan scaffolds containing microspheres as carriers for controlled transforming growth factor-β1 delivery for cartilage tissue engineering*" *Chinese Medical Journal* 2007; 120 (3); 197-203.

Several methods and reagents have been tested for their ability to crosslink chitosan and to form microspheres. Reaction of chitosan with alginate under different conditions resulted in the formation of microcapsules that had an alginate-chitosan complex membrane including either an alginate or a chitosan core, depending on the reaction conditions (Gaserod et al., loc. cit.). Chitosan microspheres were prepared from chitosan and sodium tripolyphosphate solution (Cai et al., loc. cit.).

WO 2008/103594 describes the use of chitosan and its derivatives as biomaterial for the treatment, repair and/or enhancement of bodily tissue insufficiencies of the vocal chords, muscles, ligaments and cartilage. According to the invention the use of the biomaterial produces a filling effect. Also disclosed are chitosan or chitosan-derivative gels, which optionally include chitin microspheres. In a first step of the chitin microsphere preparation, chitosan microspheres were obtained by spray-drying a chitosan solution in acetic acid/ethanol.

Several publications describe the use of citrate for the cross-linking of chitosan. However, when citrate was added to an emulsion of chitosan in acetic acid-containing solution, only irregular microparticles were formed, and microspheres could only be obtained when gelatin was added and co-emulsified (Shu, X. Z and Zhu, K. J., "*Chitosan/gelatin microspheres prepared by modified emulsification and ionotropic gelation*", *J. Microencapsulation* 2001; 18; 237). Alternatively, microspheres were obtained by dropping a solution containing chitosan and gelatin into a cold oil in order to obtain coagulation of gelatin, prior to cross-linking with citrate (Shu, X. Z and Zhu, K. J., "*Controlled drug release properties of ionically cross-linked chitosan beads: the influence of anion structure*", *Int. J. Pharm.* 2002; 233; 217). Thus, in these publications the term "chitosan microspheres" denotes microspheres comprising cross-linked chitosan and gelatin.

OBJECTS OF THE INVENTION

Accordingly, in view of the problems of the prior art, the first object of the present invention is to provide chitosan-citrate beads that are free from gelatine.

The second object of the present invention is a novel filler, which is injected below the dermis, thereby leaving no scar, rapidly restoring volume at the application site and sustaining the volume augmentation, and which does not contain collagen, which can cause allergic reactions, thereby not requiring pre-testing, such as allergic skin testing. It is also important that the particles remain evenly distributed after the injection to avoid palpable mass after the carrier is resorbed in the body. Thus, it is an object of the present invention to provide a novel filler exhibiting a long-lasting effect and far less side effects.

Another object of the present invention is to provide a novel filler composition, which, unlike conventional fillers, which contain collagen or hyaluronic acid as a major component, is not easily degraded by human enzymes or absorbed in the body, thus ensuring stable longer-lasting volume augmentation, and is cheaper than conventional fillers.

One further object of the instant invention is to provide a filler exhibiting a more improved syringeability as the conventional fillers, avoidance of aggregation of the particles in the packaging and non-homogeneous distribution of the particles at the injection site.

SUMMARY OF THE INVENTION

These and other objects are solved by chitosan beads, which consist essentially of chitosan and citrate ions, and a filler comprising such chitosan beads or chitosan beads comprising chitosan and citrate ions.

In one embodiment, the chitosan employed in the chitosan beads and/or filler according to the instant invention has a molecular weight distribution from about 50 kD to about 5000 kD.

In one embodiment of the instant invention, the chitosan employed is deacetylated to a degree from about 60% to about 100%. In a particular embodiment, the chitosan employed is deacetylated to a degree from about 70% to about 90%.

In one embodiment, the chitosan beads according to the instant invention, and/or the filler according to the instant invention comprise chitosan beads that have a mass median diameter of less than or equal to about 1500 μm determined by microscopical analysis. In a particular embodiment, the chitosan beads have a mass median diameter of between about 20 and 1000 μm, more particularly between about 20 and 500 μm, and most particularly between about 30 and 300 μm.

In one further embodiment, the present invention pertains to chitosan beads and/or a filler wherein chitosan beads and/or the filler may further comprise one or more active pharmaceutical ingredient selected from the group of anesthetics, analgesics, anti-microbials, anti-inflammatory drugs, growth factors, hormones, cosmeceuticals, vitamins, nutrients, stimulants, steroids, vasoconstrictors, anti-thrombotic agents, anti-coagulation agents, tranquilizers, muscle relaxants, antifungals, lipolytic agents and biorejuvenation agents.

In another embodiment of the instant invention, the one or more active pharmaceutical ingredient may be entrapped, bound to or encapsulated in the chitosan beads.

In one further embodiment of the instant invention, the chitosan beads and/or the filler may further comprise one or more pharmaceutical excipients selected from antioxidants, viscosity enhancers/modifiers, hydrating agents, bulking substances, tonicity agents, preservatives and surface active agents, or a mixture thereof.

The chitosan beads, including those of the herein claimed filler, are stable in form, the form stability being determined microscopically by recording the changes in spherical shape.

In one embodiment of the instant invention, the mass median diameter of the chitosan beads remains constant, i.e. within +/−20% of the starting value for the mass median diameter, for a period of at least 6 months, particularly at least 12 months, more particularly at least 24 months, and most particularly at least 36 months, at 25° C.±2° C. and 60%±5% relative humidity determined by laser diffraction technique.

In another embodiment of the present invention, the chitosan beads and/or the filler claimed herein has a shelf-life at 25° C.±2° C. and 60%±5% relative humidity of at least 6 months, particularly at least 12 months, more particularly at least 24 months, and most particularly at least 36 months.

In certain embodiments, the chitosan beads, including those of the filler, according to the instant invention have an elasticity greater 5%, a tensile strength lower 5 N, and/or a deformability greater 90%. Deformability and elasticity are determined according to the method described by Edwards-Lévy et. al. (Biomaterials 20 (1999) 2069-2084) using a texture analyzer.

In one embodiment of the instant invention, the chitosan beads are for use as drug-delivery vehicles.

In one embodiment of the instant invention, the filler is for use for aesthetic purposes.

In one further embodiment of the present invention, the filler is for use as a dermal filler.

In one embodiment of the present invention, the dermal filler is for the treatment of, or for the use in the treatment of, wrinkles and/or folds.

In another embodiment of the present invention, the filler is for the treatment of, or for the use in the treatment of, a medical condition, including lipoatrophy, gastroesophageal reflux disease (GERD), urine incontinence, vesico ureteral reflux (VUR), or a psychological condition caused by the appearance of an aesthetic deficiency, including, but not limited to, frown lines, medium depth wrinkles, such as nasolabial folds, lip augmentation, forehead wrinkles, glabellar lines, obvious mild to moderate nasal furrows and cheek wrinkles, crow's feet, perioral wrinkles, breast and acne scars.

In another embodiment of the present invention, the filler is used for the treatment of, or for the use in the treatment of, acne scars, such as by filling areas of acne scars.

The present invention further pertains to a method of treating a medical condition, including lipoatrophy, gastroesophageal reflux disease (GERD), urine incontinence, vesico ureteral reflux (VUR), or a psychological condition caused by the appearance of an aesthetic deficiency, including, but not limited to, frown lines, medium depth wrinkles, such as nasolabial folds, lip augmentation, forehead wrinkles, glabellar lines, obvious mild to moderate nasal furrows and cheek wrinkles, crow's feet, perioral wrinkles and acne scars, wherein said method comprises a step of administering a filler as claimed in the present invention to a patient in need thereof.

The present invention further pertains to a method of using a filler according to the present invention in plastic, cosmetic, dental or general surgery, in ophthalmology, in orthopedics, as products for preventing tissue adhesions, or in urology, wherein said method comprises a step of administering a filler as claimed in the present invention to a patient in need thereof.

Further, the present invention pertains to a process (i.e. a method, such as a manufacturing method) for preparing chitosan beads and/or the filler as claimed herein, wherein the process comprises a step of dropping a chitosan solution into an aqueous solution containing citrate anions.

In one embodiment in the process for preparing chitosan beads and/or the filler of the instant invention, the pH of the aqueous solution containing citrate anions is adjusted to a value from about 6 to about 11.

In one further embodiment of the present invention, the concentration of the citrate ions in the process for preparing said filler is below about 2.0 M.

In one embodiment of the present invention, the concentration of the citrate ions in the process for preparing the chitosan beads and/or the filler is between about 0.01 M and about 1.0 M.

In another embodiment of the present invention, the concentration of chitosan in the process for preparing chitosan beads and/or the filler is at maximum about 5.0 wt-% (w/w %) relative to the total weight of the composition, particularly between about 0.5 wt-% and 4 wt-%, more particularly between about 0.5 wt-% and 3 wt-%, and most particularly between about 0.5 wt-% and 2 wt-%.

In one further embodiment of the instant invention, the viscosity of the chitosan solution in the process for preparing chitosan beads and/or the filler is in the range from about 50 mPa*s to about 2000 mPa*s measured by a falling ball viscometer at 20° C., particularly between about 100 mPa*s and about 1700 mPa*s, more particularly between about 500 mPa*s and about 1500 mPa*s, and most particularly between about 750 mPa*s and about 1250 mPa*s.

In one embodiment, the pH of the chitosan solution is between about pH 1 and about pH 6, more particularly between about pH 1 and pH 5.

In another embodiment of the present invention, the aqueous solution containing citrate ions further comprises one or more active pharmaceutical ingredients selected from the group of anesthetics, analgesics, anti-microbials, anti-inflammatory drugs, growth factors, hormones, cosmeceuticals, vitamins, nutrients, stimulants, steroids, vasoconstrictors, anti-thrombotic agents, anti-coagulation agents, tranquilizers, muscle relaxants, antifungals, lipolytic agents and biorejuvenation agents.

Further, the present invention pertains to a kit comprising a filler as provided herein and an injection device. The injection device could be a syringe or an electronic injection device.

Further, the present invention pertains to an injection device comprising the filler provided herein. The injection device could be a prefilled syringe or an electronic injection device.

In another aspect, the invention relates to a method, wherein the chitosan beads cross-linked with citrate ions are redissolved after implantation, to the extent necessary, by the injection of a solution containing divalent or trivalent cations.

BRIEF DESCRIPTION OF THE FIGURES

FIG. 1. Chitosan beads cross-linked with citrate ions and stored in citrate buffer.

DETAILED DESCRIPTION OF THE INVENTION

In a first aspect, the present invention relates to chitosan beads, which consist essentially of chitosan and citrate, i.e. chitosan cross-linked with citrate ions.

The term "bead" or "beads" as used in the present invention relates to spherical particles.

In the context of the present invention, the term "chitosan beads, which consist essentially of chitosan and citrate" refers to beads that are formed from chitosan and citric acid, or a citrate salt in the presence of an acid, and wherein the resulting chitosan beads do not contain more than about 5% impurities, such as acid anions other the citrate, and/or citrate salts, particularly not more than about 2%, and even more particularly not more than 1%.

In the context of the present invention, the term "impurities" includes both (i) impurities present in the starting materials used for forming the beads, and (ii) any other substances that may otherwise provide an auxiliary function in the formation of cross-linked structures, including acid anions other the citrate, or other polymeric molecules, such as gelatine, or inert fillers. The term "impurities" does not include, however, any solvent, solvent mixture or solution, that may be entrapped in the chitosan beads. Furthermore, the term "impurities" does not include any active pharmaceutical ingredient or other substance, that is incorporated in the beads of the present invention, wherein the beads act as a vehicle for such active pharmaceutical ingredient or other substance.

Thus, the present invention relates to chitosan beads, wherein the three-dimensional network of chitosan cross-linked with citrate ions forming the bead structure consists essentially of chitosan and citrate, i.e. wherein that three-dimensional network of chitosan cross-linked with citrate ions forming the bead structure does not contain more than 5% impurities, particularly not more than about 2%, and even more particularly not more than 1%.

In a second aspect, the present invention relates to a filler comprising such chitosan beads and/or chitosan beads, wherein the chitosan beads comprise chitosan and citrate ions.

The term "filler" as used in the instant invention relates to compositions which are administered for augmentation, repair or strengthening of tissue, or for filling a bodily cavity, in a mammal. The term "mammal" as used herein refers to a human or an animal taken from the list of farm animals like horses, cattle, pigs, camels, chicken, turkey, or pets like dogs or cats.

The term "chitosan" as used in the instant invention relates to a linear polysaccharide composed of randomly distributed β-(1-4)-linked D-glucosamine (deacetylated unit) and N-acetyl-D-glucosamine (acetylated unit) and/or salts thereof.

In one embodiment, the chitosan is selected from the group of chitosan glycolate, chitosan lactate, chitosan acetate, chitosan succinate, N-(aminoalkyl) chitosan, succinyl chitosan, quateraminated chitosan, octanoyl chitosan, acetyl chitosan, thiol chitosan, trimethyl chitosan, carboxymethylchitosan, trimethyammonium chitosane, N-diethyl methyl chitosan, N-methyl chitosan, carboxymethyl chitosan, N-carboxyethyl chitosan, glycol chitosan, N-(2-hydroxy)propyl-3-trimethylammonium chitosane or mixtures thereof.

In one embodiment the chitosan is produced by deacetylation of chitin from the exoskeleton of crustaceans and cell walls of fungi or manufactured by biotechnological and/or enzymatic methods In one embodiment, the chitosan employed is deacetylated to a degree from about 60% to about 100%. A commercially available example for such a chitosan is Chitopharm® from the company Cognis, such as Chitopharm S: degree of deactylation 81%, MW 50-1000 kDa, or Chitopharm L: degree of deactylation 80%, MW 500-5000 kDa.

In one embodiment, the chitosan exhibits a molecular weight distribution from about 50 kD to about 5000 kD. A commercially available example for such a chitosan is Chitopharm® L from the company Cognis.

The term "molecular weight distribution" as used in the present invention refers to a range or distribution of the molecular weights of a population of molecules, which are not homogeneous with respect to molecular size and weight, and which thus can best be described by a range of molecular weights characterized by a lower and an upper limit, where such range covers about at least 60%, particularly at least 70%, more particularly at least 80%, and most particularly at least 90% of all molecular weights present in a given sample.

The chitosan beads are present in the filler at a concentration from about 10% (v/v) to about 95% (v/v) of total volume of the filler, as determined by determining the bead volume after sedimentation of the bead suspension in a graduated cylinder. In one embodiment, the chitosan beads are present in the filler at a concentration from about 25% to about 95% of total volume of the filler. In one further embodiment, the chitosan beads are present in the filler at a concentration from about 50% to about 95% of total volume of the filler. In another embodiment, the chitosan beads are present in the filler at a concentration from about 75% to about 95% of total volume of the filler. In one further embodiment, the chitosan beads are present in the filler at a concentration from about 85% to about 90% of total volume of the filler. The amount of chitosan beads present in the filler varies according to the size of the beads, size of the injection needle and the location of treatment.

The term "about" as used in the present invention refers to a 10% deviation from the value it is attached to.

Surprisingly, the chitosan beads prepared according to the process of the instant invention are flexible and elastic in terms of their physical properties, thus enabling an improved syringeability.

According to the present invention, the chitosan beads exhibit a particle size, measured as mass median diameter by microscopical analysis or with laser diffraction, of less than or equal to about 1500 μm. In a particular embodiment, the chitosan beads have a mass median diameter of between about 20 and 1000 μm, more particularly between about 20 and 500 μm, and most particularly between about 30 and 300 μm. The particle size can be reduced by employing known techniques, such as Air jet/Air stripping method, Jet cutter method, Vortex bowl atomizer, Vibrating nozzle device, Electrostatic device, Emulsification ("water in oil") approach, low mid and high pressure homogenization approaches. The size of the particle is adjusted according to the location of treatment. After the filler is injected the size of the chitosan beads provides fixation at the injection location and prevents undesirable migration to other parts of patient's body.

According to the instant invention the filler may comprise a medium in which the chitosan beads are suspended. Said medium may be sterile water, phosphate-buffer saline (PBS), ringer solution, isotonic saline solution (0.9%), trometamol, citrate, carbonate, acetate, borate, amino acids, diethylamine, glucono delta lactone, glycine, lactate, maleic, methanesulfonic, monoethanolamine, tartrate buffer of choice or any combination thereof. Said buffer may be citrate buffer.

In a particular embodiment, the filler according to the present invention does not comprise a chitosan gel.

The chitosan beads and/or filler as claimed in the instant invention may further comprise one or more active pharmaceutical ingredient selected from the group of anesthetics, analgesics, anti-microbials, anti-inflammatory drugs, growth factors, hormones, cosmeceuticals, vitamins, nutrients, stimulants, steroids, vasoconstrictors, anti-thrombotic agents, anti-coagulation agents, tranquilizers, muscle relaxants, antifungals, lipolytic agents and biorejuvenation agents.

The term "active pharmaceutical ingredient" refers to all structures, which are pharmacologically active, thus resulting in a pharmacological effect in mammal and all known chemical forms thereof. Examples are, but not limited to, conjugates, isomers, esters, derivatives, metabolites, residues, salts or prodrugs thereof.

Anesthetics may be, but are not limited to, local anesthetics based on esters (Procaine, Benzocaine, Chloroprocaine, Cocaine, Cyclomethycaine, Dimethodcaine, Larocaine, Propoxycaine, Proparacaine, Tretracaine) or local anesthetics based on amides (Lidocaine, Articaine, Bupivacaine, Carticaine, Cinchocaine, Etidocaine, Levobupivacaine, Mepivacaine, Piperocaine, Prilocaine, Ropivacaine, Trimecaine). A suitable concentration for the anesthetic is from about 0.01% to 6% based on the total weight of the composition and the agent selected.

Analgesics may be, but are not limited to, paracetamol, ibuprofen, diclofenac, naproxen, aspirin, celecoxib, etoricoxib, lumiracoxib, parecoxib, rofecoxib, valdecoxib, nimesulid.

Antimicrobials may be, but are not limited to, antibiotics (amikacin, gentamycin, neomycin, tobramycin, kanamycin, meropenem, imipenem, cefaclor), antivirals (abacavir, aciclovir, amantadine, boceprevir, cidofovir, darunavir, edoxudine, famciclovir, ganciclovir, immunovir, inosine, interferon, lamivudine, nexavir, oseltamivir, penciclovir, ribavirin, rimantadine, viramidine, zidovudine) and antifungals (Miconazole, ketoconazole, itraconazole, clotrimazole, econazole, fluconazole, voriconazole, abafungin, naftifine, caspofungin, micafungin, benzoic acid, griseofulvin).

Anti-inflammatory drugs may be, but are not limited to, zinc salts, including zinc salts of polysaccharide acids, such as hyaluronic acid.

In one embodiment of the instant invention, the one or more active pharmaceutical ingredients are entrapped in the chitosan beads.

In one embodiment of the instant invention, living cells, e.g. autologous stem cells, are entrapped in the chitosan beads.

In one embodiment of the instant invention, a polysaccharide is entrapped in the chitosan beads.

In one embodiment of the instant invention, proteins or peptides, e.g. adhesion proteins, granulocyte-colony stimulating factors, erythropoietin, bone morphogenic protein, tissue plasminogen activator, are entrapped in the chitosan beads.

In one further embodiment of the present invention, the filler further comprises one or more pharmaceutical excipients selected from antioxidants, viscosity enhancers/modifiers, hydrating agents, bulking substances, tonicity agents, preservatives and surface active agents, or a mixture thereof.

Antioxidants may be, but are not limited to, vitamin E, vitamin C, glutathione coenzyme Q, resveratrol, bisulfite sodium, butylated hydroxyl anisole/toluene, cysteinate, dithionite sodium, gentisic acid, glutamate, formaldehyde sulfoxylate sodium, metabisulfite sodium, monothiogylcerol, propyl gallate, sulfite sodium, thiogycolate sodium, flavonoids, catalase, lycopene, carotenes, lutein, superoxide dismutase and peroxidases or mixtures thereof.

Viscosity enhancers may be, but are not limited to, glycerol, xanthene gum, polyethylene glycol (PEG), alginate, carbomers, cellulose derivatives, dextrans, and carrageenan, starches, gum, acacia, tragacanth, gelatin, polyvinylpyrrolidone, albumin, dextran or mixtures thereof.

Surface active agents may be, but are not limited to, polysorbate 20, polysorbate 80, polysorbate 40, polysorbate 60, polysorbate 65, Pluronic F68, Cetrimoniumbromid, Cetylpyridiniumchlorid, Brij 72, Brij 30, Brij 35, deoxycholate, lecithine, tocopheryl polyethylene glycol succinate or mixtures thereof.

Bulking substances or tonicity modifiers may be substances such as glycerol, lactose, mannitol, dextrose, sodium or potassium chloride, sodium sulphate and sorbitol, in general at a concentration up to 5% depending upon the chosen substance and the composition of the formulation.

In certain embodiments of the present invention, the chitosan beads are stable in form, such form stability being determined microscopically by recording the changes in spherical shape.

The stability is further determined by measuring periodically the mass median diameter of the chitosan beads. In one embodiment of the invention, the mass median diameter of the chitosan beads remains constant, i.e. within +/−20% of the starting value for the mass median diameter, for a period of at least 6 months, particularly at least 12 months, more particularly at least 24 months, and most particularly at least 36 months, at 25° C.±2° C. and 60%±5% relative humidity determined by laser diffraction technique.

In one further embodiment, the filler has a shelf-life at 25° C.±2° C. and 60%±5% relative humidity of at least 6 months, particularly at least 12 months, more particularly at least 24 months, and most particularly at least 36 months.

In certain embodiments, the chitosan beads, including those of the filler, according to the instant invention have an elasticity greater 5%, a tensile strength lower 5 N, and/or a deformability greater 90%. Deformability and elasticity are determined according to the method described by Edwards-Lévy et. al. (Biomaterials 20 (1999) 2069-2084) using a texture analyzer.

In certain embodiments, the filler of the instant invention is for use for aesthetic purposes.

In the context of the present invention, the term "use for aesthetic purposes" refers to non-medical uses.

In one embodiment of the present invention, the filler is a dermal filler

In another embodiment, the dermal filler is for the treatment of wrinkles and/or folds.

In the context of the present invention, the term "treatment of wrinkles and/or folds" refers to non-medical treatments.

Wrinkles that may be treated by employing the filler according to the instant invention include, but are not limited to, frown lines, medium depth wrinkles, such as nasolabial folds, lip augmentation, forehead wrinkles, glabellar lines, obvious mild to moderate nasal furrows and cheek wrinkles, crow's feet, perioral wrinkles and acne scars.

In another embodiment of the present invention, the filler is for the treatment of, or for use in the treatment of, a medical condition, including lipoatrophy, gastroesophageal reflux disease (GERD), urine incontinence, vesico ureteral reflux (VUR), and the treatment of a psychological condition caused by the appearance of an aesthetic deficiency, including, but not limited to, frown lines, medium depth wrinkles, such as nasolabial folds, lip augmentation, forehead wrinkles, glabellar lines, obvious mild to moderate nasal furrows and cheek wrinkles, crow's feet, perioral wrinkles and acne scars.

In another embodiment of the present invention, the filler is for use in plastic, cosmetic, dental or general surgery, in ophthalmology, in orthopedics, for preventing tissue adhesions, or in urology.

The present invention further pertains to methods of using the chitosan beads and/or the fillers of the present invention for aesthetic purposes, including the use as dermal filler, such as in the treatment of wrinkles and/or folds.

The present invention further pertains to methods of using the chitosan beads and/or the fillers of the present invention for the therapeutic treatment of a patient in need thereof, such as in the treatment of lipoatrophy, gastroesophageal reflux disease (GERD), urine incontinence, vesico ureteral reflux (VUR), and the treatment of a psychological condition caused by the appearance of an aesthetic deficiency, including, but not limited to, frown lines, medium depth wrinkles, such as nasolabial folds, lip augmentation, forehead wrinkles, glabellar lines, obvious mild to moderate nasal furrows and cheek wrinkles, crow's feet and perioral wrinkles.

The present invention further pertains to a method of treating a medical condition, including lipoatrophy, gastroesophageal reflux disease (GERD), urine incontinence, vesico ureteral reflux (VUR), or a psychological condition caused by the appearance of an aesthetic deficiency, including, but not limited to, frown lines, medium depth wrinkles, such as nasolabial folds, lip augmentation, forehead wrinkles, glabellar lines, obvious mild to moderate nasal furrows and cheek wrinkles, crow's feet, perioral wrinkles and acne scars, wherein said method comprises a step of administering a filler as claimed in the present invention to a patient in need thereof The present invention further pertains to a method of using a filler according to the present invention in plastic, cosmetic, dental or general surgery, in ophthalmology, in orthopedics, as products for preventing tissue adhesions, or in urology, wherein said method comprises a step of administering a filler as claimed in the present invention to a patient in need thereof.

The present invention further pertains to a process for preparing chitosan beads and/or a filler according to the invention, which comprises a step of dropping a chitosan solution into an aqueous solution containing citrate anions.

In one embodiment, the pH of the aqueous solution containing citrate anions is adjusted to a value from about 5 to about 10.

In one further embodiment, the concentration of the citrate ions is below about 2.0 M.

In another embodiment, the concentration of citrate ions is between about 0.01 M and about 1.0 M.

In another embodiment of the present invention, the concentration of chitosan in the process for preparing chitosan beads and/or the filler is at maximum about 5.0 wt-% (w/w %) relative to the total weight of the composition, particularly between about 0.5 wt-% and 4 wt-%, more particularly between about 0.5 wt-% and 3 wt-%, and most particularly between about 0.5 wt-% and 2 wt-%.

In one further embodiment of the instant invention, the viscosity of the chitosan solution in the process for preparing chitosan beads and/or the filler is in the range from about 50 mPa*s to about 2000 mPa*s measured by a falling ball viscometer at 20° C., particularly between about 100 mPa*s and about 1700 mPa*s, more particularly between about 500 mPa*s and about 1500 mPa*s, and most particularly between about 750 mPa*s and about 1250 mPa*s.

In one further embodiment of the process of the present invention, the aqueous solution containing citrate ions may further comprise one or more active pharmaceutical ingredient selected from the group of anesthetics, analgesics, antimicrobials, anti-inflammatory drugs, growth factors, hormones, cosmeceuticals, vitamins, nutrients, stimulants, steroids, vasoconstrictors, anti-thrombotic agents, anti-coagulation agents, tranquilizers, muscle relaxants, antifungals, lipolytic agents and biorejuvenation agents.

The present invention further pertains to a kit comprising (a) the filler as disclosed herein, and (b) an injection device. In one embodiment, the injection device comprises a 25- to 32-gauge needle. The size of the needle will be determined by the filler composition, the depth of the injection site and the injection volume. In certain embodiments, the injection device is disposable. In one embodiment, the injection device is made of sterile glass.

The present invention further pertains to an injection device comprising chitosan beads and/or a filler as disclosed herein. In one embodiment, the injection device may comprise a 25- to 32-gauge needle. The size of the needle will be determined by the filler composition, the depth of the injection site and the injection volume. In certain embodiments, the injection device is disposable. In one embodiment, the injection device may be made of sterile glass.

In certain embodiments, the injection device and the chitosan beads and/or filler provided herein are both sterile and non-pyrogenic e.g. containing less than 10 EU (Endotoxin Unit, a standard measure) per dose or application. The methods of achieving the sterility of the chitosan beads and/or filler are those known to the person skilled in the art.

Isotonicity of the chitosan beads and/or filler may be accomplished by employing sodium chloride, or other pharmaceutically acceptable agents such as dextrose.

A pharmaceutically acceptable preservative may be employed to improve the shelf-life of the filler. The preservative may be, but is not limited to, benzalkonium chloride, thiomersal, parabens, chlorobutanol, benzethonium chloride, m-cresol, phenol, 2-phenoxyethanol, phenyl mercuric nitrate or benzyl alcohol. The suitable concentration of the preservative agent is from about 0.001% to 5% based on the total weight of the composition and the agent selected.

In another aspect, the invention relates to a method, wherein the chitosan beads cross-linked with citrate ions are redissolved after implantation, to the extent necessary, by the injection of a solution containing divalent or trivalent cations.

In another embodiment, the injection volume of the dispersed beads is between 0.1 and 100 ml, particular between 0.1 and 50 ml, more particular between 0.1 and 30, 0.1 and 20, or 0.1 and 10 ml, and most particular between 0.1 and 5, 0.1 and 2, or 0.1 and 1 ml. Alternatively, the volume can be higher than 100 ml if larger areas are augmented.

The invention is now described with reference to the following examples. These examples are provided for the purpose of illustration only and the invention should not be construed as being limited to these examples, but rather should be construed to encompass any and all variations which become evident as a result of the teaching provided herein. The following materials and methods are provided with respect to the subsequent examples but do not limit a multiplicity of materials and methodologies encompassed by the present invention.

EXAMPLES

Example 1

Manufacturing of Chitosan Beads and/or a Filler Comprising Such Beads

Chitosan (Chitopharm L) is dispersed in deionized water. The appropriate amount of acid is added to the dispersion under constant stirring (0.05 mol per 10 g of chitosan). The dispersion is stirred until a clear solution is obtained. Having obtained a clear solution the pH of the obtained chitosan solution is stabilized from pH 1 to 5. With the help of a 30 Gauge syringe the chitosan solution is dropped into the following solutions having a pH from 5 to 11 and the obtained beads are let for 1 h in solution.

|  | Crosslinking media | | | |
| --- | --- | --- | --- | --- |
|  | 1M Citrate | 1M citrate | 1M citrate | 1M citrate |
| pH of the media | 8 | 9 | 10 | 11 |
| Observation after dropping | Formation of circular beads | Formation of circular beads | Formation of circular beads | Formation of circular beads |
| Observation after 1 h cross-linking | Elastic, flexible beads | Elastic, flexible beads | Less flexible, more rigid beads | Less flexible, more rigid beads |

The obtained chitosan beads were investigated by employing a microscope (Mikroskop Nikon Eclipse E600W). FIG. 1 shows chitosan beads cross-linked with citrate ions and stored in citrate buffer. The beads are perfect in shape, i.e. being circular. Bead size is 1.0 to 1.5 mm.

Example 2

Loading of Chitosan Beads with Active Pharmaceutical Ingredients

Chitosan is dispersed in deionized water. The appropriate amount of acid is added to the dispersion under a constant stirring. The dispersion is stirred until a clear solution is obtained. As a second solution, lidocaine hydrochloride USP (2% weight per weight) is dissolved in the chitosan solution. With the help of a 30 Gauge syringe the chitosan lidocaine solution is dropped into the following solutions having a pH from 1 to 5 and the obtained beads with lidocaine encapsulated are let for 1 h in solution.

Example 3

Administration of the Filler Comprising Chitosan Beads

The filler prepared according to example 1 is injected to a 50-year old female patient into nasolabial folds.

Example 4

Determination of the Elasticity and Flexibility of Chitosan Beads

Chitosan citrate beads were prepared according to the method described in example 1 at pH 8.5. Ten randomly chosen beads were selected for each experiment and the mean value and standard deviation were calculated.

Elasticity and flexibility were determined using a Texture Analyser TA.XT plus, Stable Micro Systems Ltd according to the method described by Edwards-Lévy et. al. (Biomaterials 20 (1999) 2069-2084) with some minor modifications. For the rupture study and deformability study a single chitosan bead in a Petri dish was placed under a piston, the piston went down at the rate of 1.0 mm/s, until a resistance force of 2.5 g was detected meaning the contact of the piston with the top of the bead. Then, the piston went down at a constant rate of 0.5 mm/s until it hit the bottom of the Petri dish, while the force opposed to the bead as a function of the displacement was determined. The rupture force as the initial force recognized when the piston reached the bead was calculated and the deformability expressed as the percentage of the total height of the sample that the piston reached before breakage. Tensile strength of the chitosan beads was 2.0±0.3 N, Deformability was 96±2%.

Elasticity of the chitosan citrate beads was determined and calculated as the ratio of the force opposed by the bead after 10 s to the instantaneous resistance strength of the bead. The bead was placed under the piston, which went down at a rate of 2.0 mm/s until it reached 30% of the total height of the bead. Then, the piston stayed motionless at this position for 10 s and finally returned to its initial position. The elasticity of the beads was 7.2±1.7%.

The invention claimed is:

1. Chitosan beads consisting essentially of chitosan and citrate ions, wherein the chitosan has an average molecular weight of from about 50 kD to about 5000 kD and is deacetylated to a degree of from about 70% to about 100%, wherein the chitosan beads exhibit a mass median diameter of less than or equal to 1500 μm as determined by microscopical analysis, and wherein the mass median diameter of a chitosan bead remains less than or equal to 1500 μm for a period of 6 months at 25° C.±2° C. and 60%±5% relative humidity as determined by laser diffraction analysis.

2. The chitosan beads of claim 1, wherein the chitosan beads have a shelf-life of 6 months at 25° C.±2° C. and 60%±5% relative humidity.

3. Chitosan beads consisting essentially of chitosan and citrate ions, wherein the chitosan has an average molecular weight of from about 50 kD to about 5000 kD and is deacetylated to a degree of from about 70% to about 100%, wherein the chitosan beads are in the form of a filler composition, wherein the filler composition further comprises a polysaccharide, and/or (ii) one or more active pharmaceutical ingredients selected from the group consisting of anesthetics, analgesics, anti-microbials, anti-inflammatory drugs, growth factors, hormones, cosmeceuticals, vitamins, nutrients, stimulants, steroids, vasoconstrictors, anti-thrombotic agents, anti-coagulation agents, tranquilizers, muscle relaxants, antifungals, lipolytic agents, biorejuvenation agents, antioxidants, viscosity enhancers/modifiers, hydrating agents, bulking substances, tonicity agents, preservatives and surface active agents, and mixtures thereof, wherein the filler composition has a shelf-life of 6 months at 25° C.±2° C. and 60%±5% relative humidity.

4. The chitosan beads of claim 3 in the form of a filler composition, wherein the filler composition further comprises a polysaccharide and/or one or more active pharmaceutical ingredients, wherein the polysaccharide and/or one or more active pharmaceutical ingredients is/are entrapped in the chitosan beads.

\* \* \* \* \*

UNITED STATES PATENT AND TRADEMARK OFFICE
CERTIFICATE OF CORRECTION

| | | |
|---|---|---|
| PATENT NO. | : 8,865,879 B2 | Page 1 of 1 |
| APPLICATION NO. | : 13/639004 | |
| DATED | : October 21, 2014 | |
| INVENTOR(S) | : Kevin Kiehm et al. | |

It is certified that error appears in the above-identified patent and that said Letters Patent is hereby corrected as shown below:

Title Page item (56) line 1, under Foreign Patent Documents: "CN 101245238" should be -- CN 101245236 --.

In the Claims,
Column 12, line 62: "comprises a" should be -- comprises (i) a --.

Signed and Sealed this
Twentieth Day of January, 2015

Michelle K. Lee
*Deputy Director of the United States Patent and Trademark Office*